United States Patent [19]

Dalamagas et al.

[11] Patent Number: 5,271,413
[45] Date of Patent: Dec. 21, 1993

[54] METHOD TO SENSE THE TISSUE FOR INJECTION FROM A HYPODERMIC NEEDLE

[76] Inventors: Photios P. Dalamagas, 74 Amston Rd., Colchester, Conn. 06415; Mark A. Sapia, 5 Ann La., Canton, Conn. 06022

[21] Appl. No.: 917,184

[22] Filed: Jul. 22, 1992

[51] Int. Cl.⁵ .................................. A61B 5/05
[52] U.S. Cl. ........................... 128/734; 607/116
[58] Field of Search .................... 128/733–735, 128/784; 604/116; 606/41, 44

[56] References Cited

U.S. PATENT DOCUMENTS

| | | | |
|---|---|---|---|
| 4,515,168 | 5/1985 | Chester et al. | 128/784 |
| 4,690,152 | 9/1987 | Juncosa | 128/734 |
| 4,805,621 | 2/1989 | Heinze et al. | 128/419 PG |
| 4,823,797 | 4/1989 | Heinze et al. | 128/419 PG |
| 4,836,214 | 6/1989 | Sramek | 128/734 |
| 4,883,053 | 11/1989 | Simon | 604/116 |
| 5,080,104 | 1/1992 | Marks et al. | 604/116 |

FOREIGN PATENT DOCUMENTS 2136575 9/1984 United Kingdom ............... 128/734

*Primary Examiner*—Max Hindenburg
*Attorney, Agent, or Firm*—L. James Ristas

[57] ABSTRACT

Many pharmaceuticals require a specific tissue for injection, such as adipose or muscle, to optimize the effect of the drug. This is important to achieve the desired bioavailability of the injected substance. In some cases, intravenous injections are desired over subcutaneous and intramuscular. The invention is a bioimpedance method and apparatus for sensing a hypodermic needle's transition from subcutaneous adipose to muscle tissue. The invention could also be used to sense a vascular transition. The sensing can be integrated into instrumentation that identifies the tissue or simply signals that the transition has occurred. The physician or nurse could then confidently inject the medication into the intended tissue.

17 Claims, 6 Drawing Sheets

METHOD TO SENSE THE TISSUE FOR INJECTION FROM A HYPODERMIC NEEDLE

BACKGROUND OF THE INVENTION

This invention generally relates to routine subcutaneous hypodermic injections, specifically to the identification of the injection tissue, whether intramuscular, subcutaneous adipose or intravascular.

Pharmaceutical companies recommend the tissue of injection for various drugs that are given by hypodermic needle. The purpose is to optimize the intended bioavailability of the injected medication. For example, antibiotics are generally recommended to be injected intramuscularly to assure rapid and complete bioavailability. In other cases, drugs such as insulin are generally desired to be injected into adipose tissue to slow the bioavailability. It is important to avoid accidental insulin injections into the non-recommended tissue. This would inevitably result in variability in blood glucose control. Additionally, some drugs may be required to be injected intravascularly. Currently, there is no known method that reliably determines which tissue a drug is being administered to. To achieve this objective, it is necessary to devise a method for reliably sensing a transition of the needle tip between tissue types during insertion.

The consequences of not adhering to the recommended injection tissue can lead to adverse physiological effects. For example, abscesses, induration, persistent local pain, and hematoma have been extensively reported. The problem of missing the intended injection tissue has been reported to be more prevalent in pediatric patients.

Currently, intramuscular injections are performed by subjectively feeling the needle transition into muscle. Although there may be a definite transition that can be sensed by touch, it is likely that the transition will not be felt. This is particularly a problem with obese, pediatric and geriatric patients. Clearly, there is a need for a reliable device to sense the transition and eliminate subjectivity.

Another known method for determining the location of a fat-muscle interface is to use ultrasound. This method has been used for several years on livestock to determine the fat layer thickness on animals. Unfortunately, this method would be cumbersome to implement for the purpose of sensing a hypodermic needle transitioning into muscle. The reason is primarily the need to use a separate ultrasonic transducer to provide depth information. This information can then be translated to needle depth. Thus, it is an indirect method and consequently not desirable for this application.

SUMMARY OF THE INVENTION

It is the object of the present invention to provide a means for sensing when a hypodermic needle has reached its desired tissue of injection. For example, going from subcutaneous adipose into muscle. This object is accomplished by sensing bioimpedance changes due to needle transitions without the need for any additional invasive procedure other than the needle itself. The needle, therefore, is the sensing electrode that is connected to bioimpedance measurement circuitry. This bioimpedance method will work using either direct current (DC) or alternating current (AC). Using AC for this invention is desirable over DC to avoid the capacitive charging effects that may occur with DC. An additional advantage of using AC is that signal phase can be used to sense the transition. A bioimpedance sensing circuit connected to the syringe needle and reference electrode, provides the output that signals the needle is in the appropriate tissue.

Another object is that the device should not signal a transition until the needle is at least 2 to 5 millimeters into the intended tissue. This will assure that the injection is completely administered into the intended tissue. This object is accomplished by the fact that the bioimpedance measurement requires a significant surface area of electrode contact to the different tissue layer before there is a substantial change in overall impedance.

In summary, this invention is a device and method which provides a means for reliably injecting pharmaceuticals into the intended tissue. The invention is also a new use of bioimpedance measurement. Bioimpedance is used for the purpose of identifying the tissue surrounding the needle tip. Additionally, the invention is an improvement over the currently used method of subjectively feeling needle transitions.

BRIEF DESCRIPTION OF THE DRAWINGS

These and other objects and advantages are accomplished with the preferred embodiment of the invention as described below with reference to the accompanying drawings in which.

DESCRIPTION OF THE PREFERRED EMBODIMENT

Figure 1:
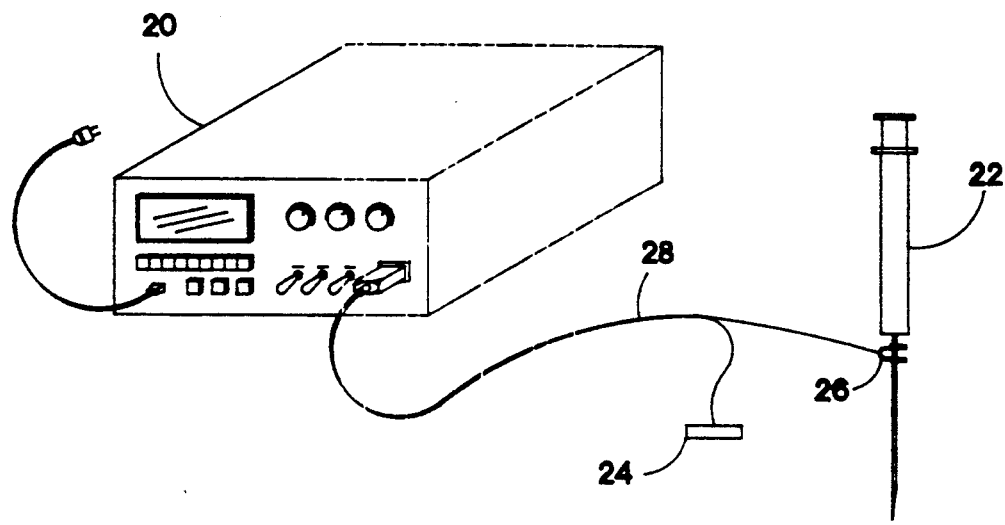
FIG. 1 is an illustration of how the bioimpedance apparatus would be implemented to sense a hypodermic needle's transition between various tissue types.
Figure 1:
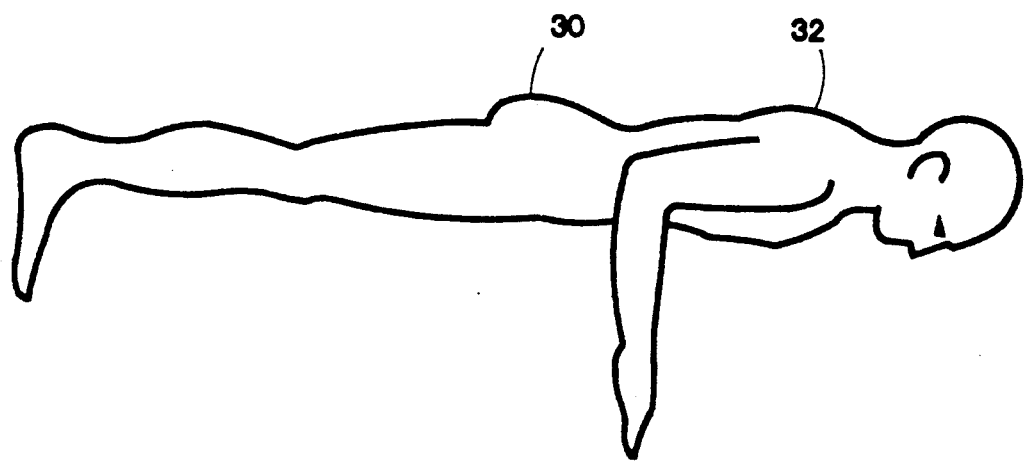

4 FIG. 1 shows the apparatus instrumentation 20 for detection of the injection tissue connected to a syringe 22 and reference electrode 24. The connection to the syringe needle is accomplished by a clip 26, preferably disposable. The patient cable 28 is a two-conductor "Y" cable that connects to the electrode and needle. The typical body sites for application would be the gluteal region 30 or the deltoid region 32 of the patient.

Figure 2:
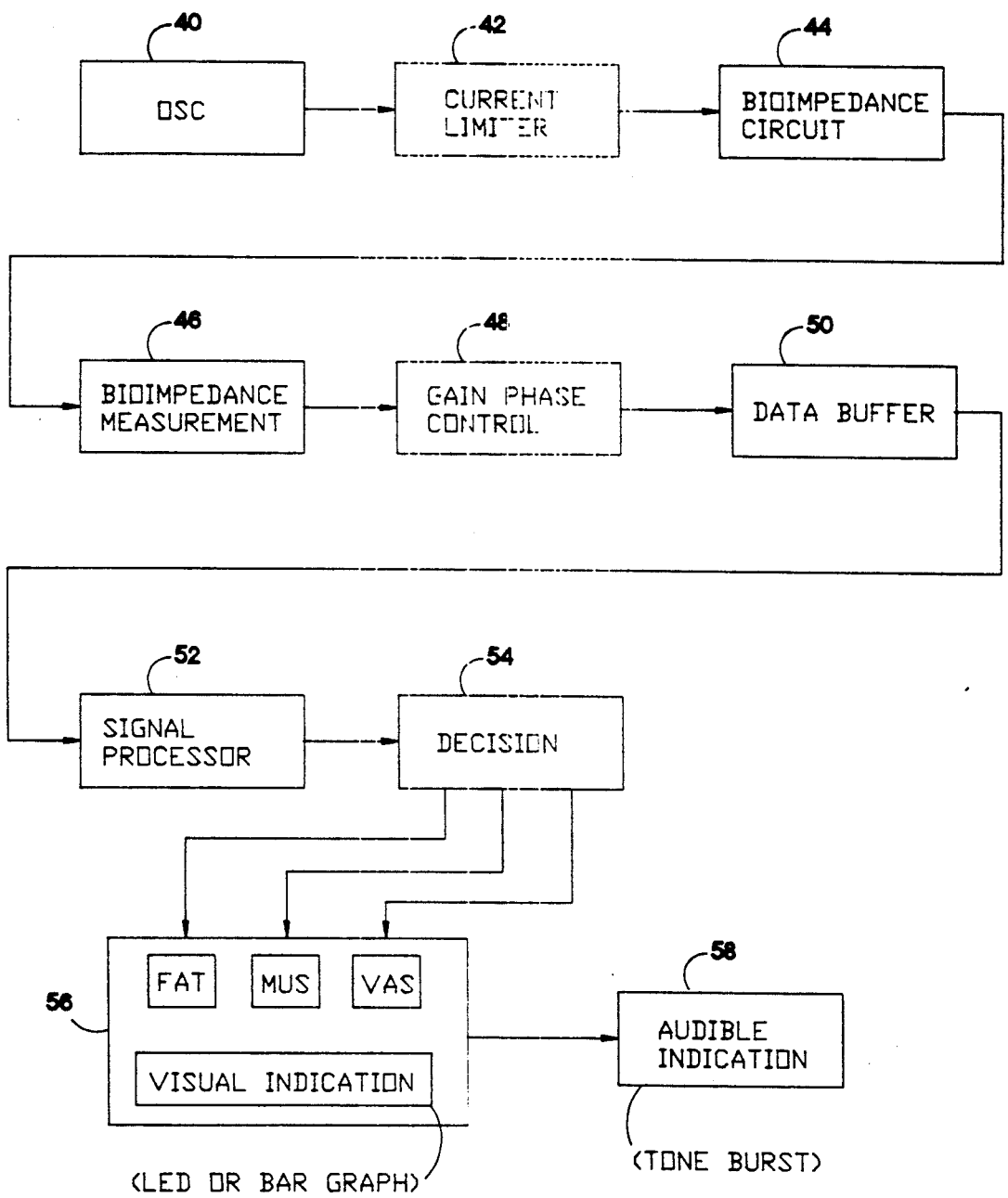
FIG. 2 is a block diagram of the bioimpedance measuring apparatus constructed in accordance with the principles of the present invention.

FIG. 2 shows the block diagram of the instrumentation circuitry. The oscillator 40 generates the electrical signals at some frequency or frequencies which are impressed on the patient. The current limiter 42 is a means for limiting the current of the electrical signals to a universally safe level. The bioimpedance circuit 44 establishes the electrical circuit through the tissue between the electrode and the needle. The bioimpedance measurement 46 is accomplished by quadrature sampling to obtain both resistive and reactive components of complex impedance. Gain and phase adjustments can then be made to the measured impedance via the gain and phase controls 48. A data buffer 50 can then be used to digitize and store an appropriate amount of measured impedance data for signal processing. The signal processor 52 operates on the impedance data to provide the information necessary for a decision. Decision logic can then be applied 54 to determine the tissue of injection. This decision can then be routed to the corresponding visual indicator 56 and/or the corresponding audible indicator 58.

Figure 3:
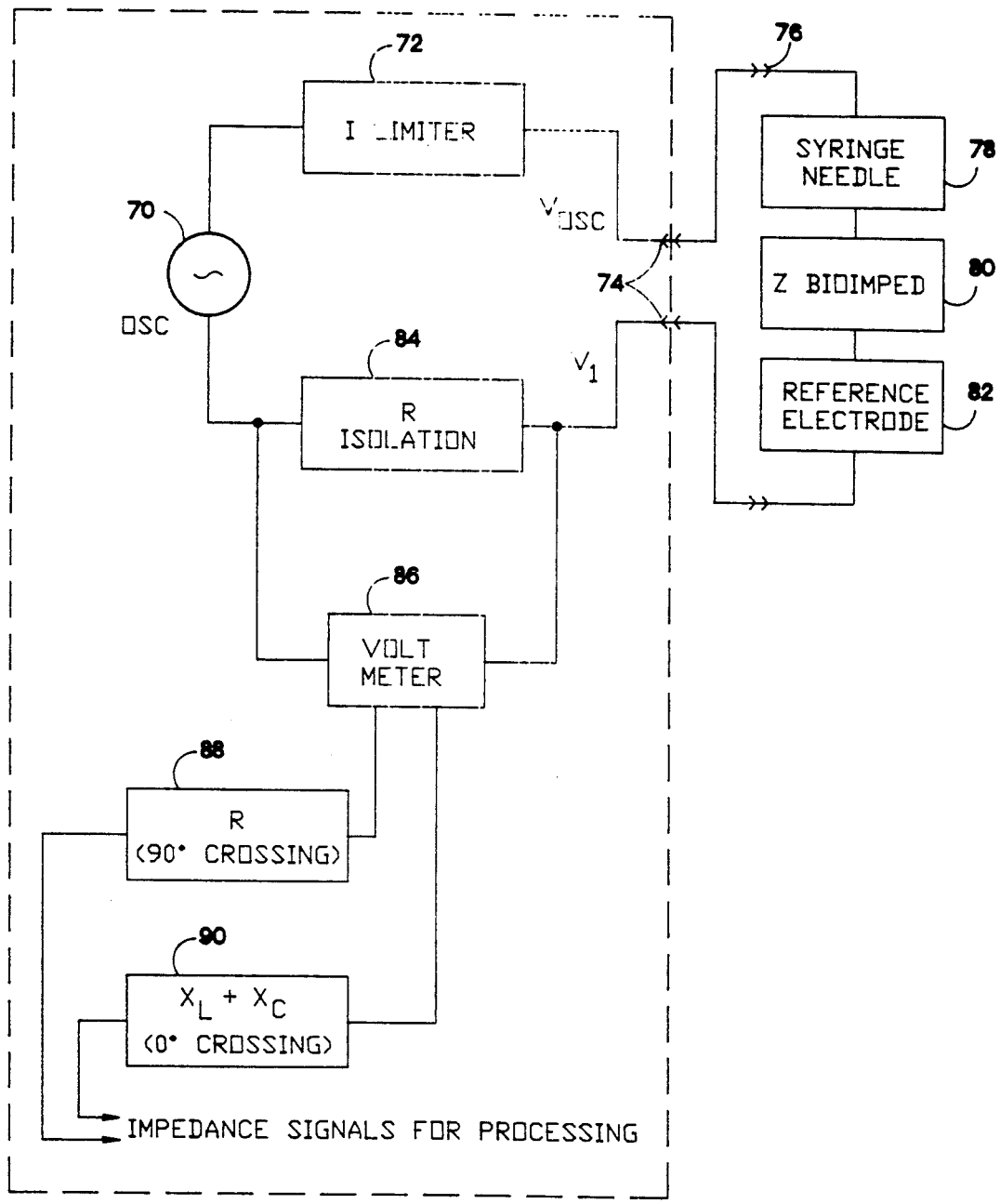
FIG. 3 is a block diagram of the circuit model of the instrumentation used to establish the bioimpedance measurement.

FIG. 3 shows a block diagram of the bioimpedance measurement circuit. The oscillator 70 is connected to a current limiter 72 which limits the current that can be delivered to the patient's tissue. It is then connected to the front panel where the external cabling plugs in 74. The external cables are connected to the syringe and electrode. A metal clip 76 will be used to connect the cable to the syringe 78 which will secure the cable to the needle. The syringe makes contact by insertion into the tissue. The tissue has an impedance(Z) 80. The tissue impedance is measured between the needle and a reference electrode 82. In order to obtain both the real and imaginary components of the impedance, the voltage is measured twice across the isolation resistor 84. These voltage measurements provide a linear relationship with the impedance of the needle-tissue-electrode circuit. The isolation resistor functions to isolate the measurements from the oscillator. Two measurements are taken with a volt meter 86, one at the zero (0°) crossing and one at the 90° crossing of the oscillator. This is a quadrature sampling technique used to obtain complex impedance. The 0° crossing measurement corresponds to the imaginary part of the impedance 88 and the 90° crossing measurement corresponds to the real part of the impedance 90.

Figure 4A:
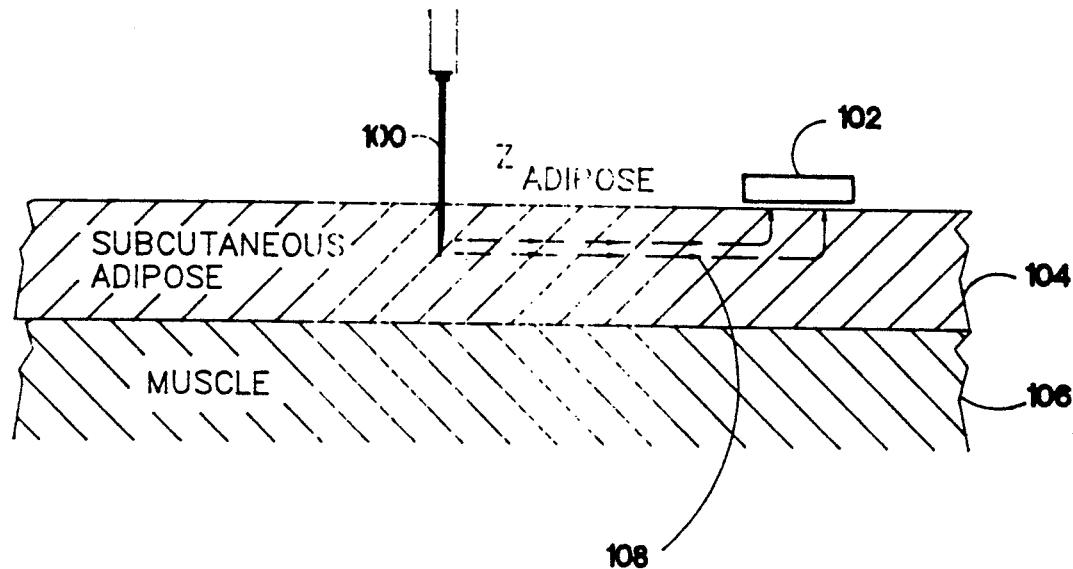
FIGS. 4A and 4B are illustrations that show how the change in bioimpedance is sensed due to a tissue transition.
Figure 4B:
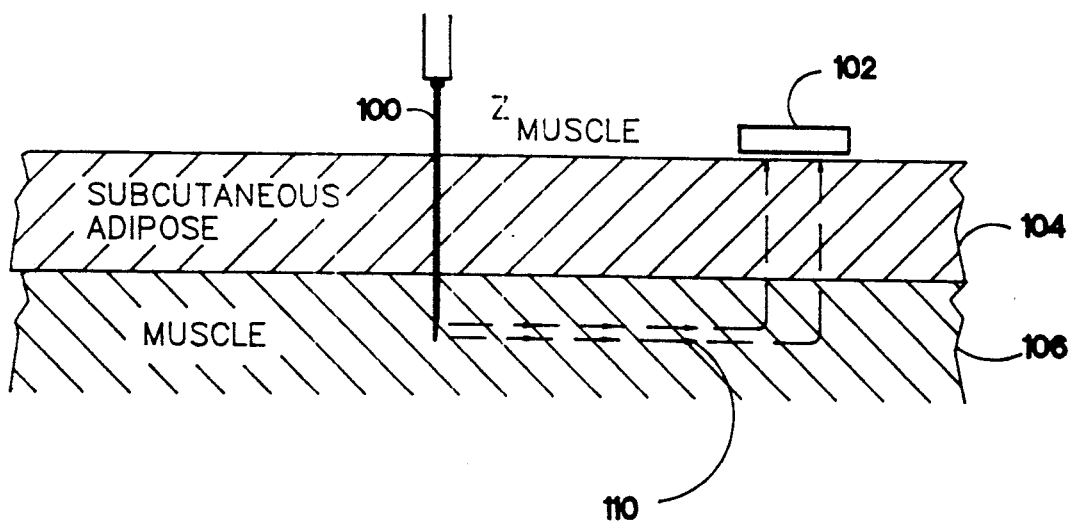

FIG. 4 shows how the change in bioimpedance is sensed. When the needle 100 is inserted into subcutaneous adipose 104, there is an impedance through the adipose between the needle and reference electrode 102. The impedance depends on the distance between the needle and electrode, the conductivity of the tissue (adipose) and the surface area available on the needle and electrode to conduct current. These items affect the current flow through adipose 108. In the drawing on the right, the needle is shown to penetrate into the muscle tissue 106. Since the conductivity of muscle tissue is much greater than adipose, the current will prefer to flow 110 through the muscle. However, there is still current flow through the thickness of adipose. Thus, for this invention to perform its stated objectives, the distance between the needle and the electrode must be substantially greater than the thickness of adipose directly beneath the electrode, say 2 to 1 as a minimum to assure reliable detection of the needle's transition. For routine injections, a template could be used to establish a minimum distance between the needle and electrode to fulfill this requirement.

Figure 5A:
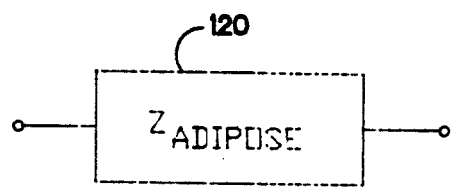
FIGS. 5A and 5B are the equivalent circuit models for each of the two illustrations in FIGS. 4A and 4B.
Figure 5B:
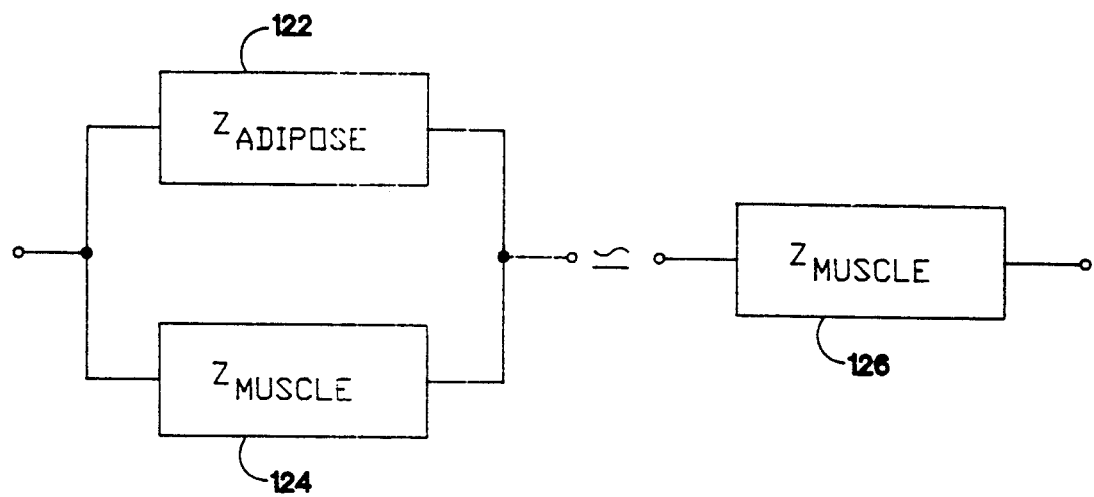

FIG. 5 shows the equivalent circuit models for each of the two illustrations above in FIG. 4. With the needle inserted into the adipose only, the corresponding circuit is the impedance of the adipose between the needle and electrode 120. With the needle inserted through the adipose and into the muscle tissue, the corresponding circuit is the parallel combination of the adipose impedance 122 and muscle impedance 124. Since the muscle impedance is much less than adipose impedance, the impedance of the parallel combination is approximately equal to that of the muscle only 126.

Figure 6:
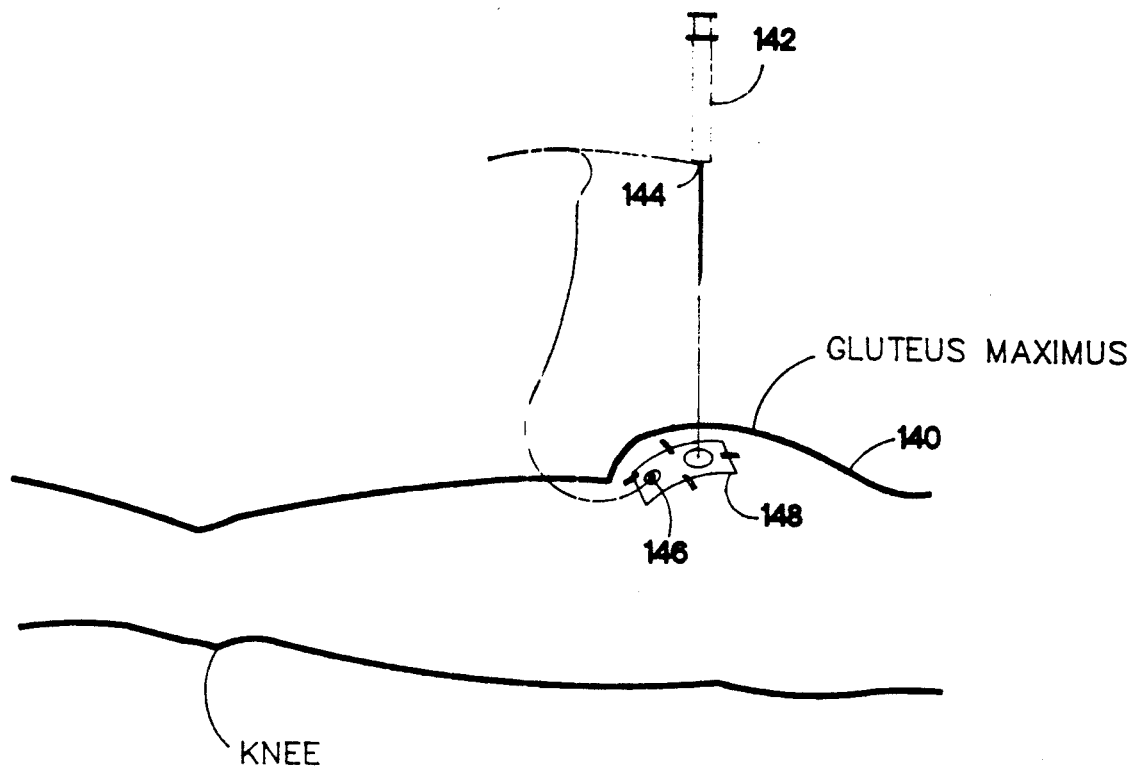
FIG. 6 is an illustration of how the device would be used with a patient. Also shown in FIG. 6 is the use of a template to control the placement of the syringe relative to the reference electrode.

FIG. 6 is an illustration of how the device would be used with a patient who requires an injection of medication to be administered into the gluteal region 140. The syringe 142 is shown with a lead connected to the upper portion of the needle 144. The electrode 146 is typically an ECG type which adheres to the body with a conductive gel for low impedance coupling to the body. A template 148 is shown which provides adequate spacing between the electrode and needle injection site to assure optimum detection sensitivity.

We claim:

1. A method for identifying which of a plurality of subcutaneous tissue types a needle has penetrated at a target location through the outer surface of a body, comprising:
   placing a reference electrode on the surface of the body at a reference location spaced from the target location;
   applying an electrical source signal to one of the reference electrode and the needle with an electrical signal source means;
   connecting electrical signal processing means to the reference electrode and to the needle, said signal processing means including means for sensing the impedance encountered by said source signal in passing between the needle and the reference electrode;
   inserting the needle into the body at the target location while monitoring the sensed impedance; and
   in response to variations in the impedance during the step of inserting the needle, generating an output signal indicative of the type of subcutaneous tissue into which the needle has penetrated.

2. The method of claim 1, wherein the step of applying an electrical source signal includes applying one of an oscillating current or oscillating voltage.

3. The method of claim 2, wherein
   the signal processing means includes an isolation resister connected between the oscillating electrical signal source means and the reference electrode, and
   the step of sensing impedance includes determining the complex impedance by measuring the voltage across the isolation resistor with quadrature sampling.

4. The method of claim 1, wherein,
   muscle tissue is beneath adipose tissue at the target location, and
   the step of generating an output signal includes generating an output signal indicative of adipose tissue when the sensed impedance is relatively high and generating an output signal indicative of muscle tissue when the sensed impedance is relatively low.

5. The method of claim 4, wherein the step of inserting the needle includes inserting the needle at a target location that is spaced from the reference location a distance that is at least about two times the thickness of the adipose tissue at the reference location.

6. The method of claim 1, including the step of placing a template on the body surface such that a first opening in the template is situated at the target location and a second opening in the template defines the reference location.

7. A method for injecting a substance through a syringe needle into a preselected one of a plurality of subcutaneous tissue types beneath a target location on a body surface, comprising:

placing a reference electrode of the surface of the body at a reference location spaced from the target location;

applying an electrical source signal to one of the reference electrode and the needle with an electrical signal source means;

connecting electrical signal processing means to the reference electrode and to the signal source means, said processing means including means for sensing the impedance encountered by said source signal in passing between the needle and the reference electrode;

inserting the needle into the body at the target location while monitoring the sensed impedance;

in response to variations in the impedance during the step of inserting the needle, generating an output signal indicative of the type of subcutaneous tissue into which the needle has penetrated; and injecting the substance when the needle is in the preselected subcutaneous tissue as indicated by the output signal.

8. The method of claim 7, wherein the step of applying an electrical source signal includes applying one of an oscillating current or oscillating voltage source to the needle.

9. The method of claim 8, wherein the signal processing means includes an isolation resistor connected between the oscillating source and the reference electrode, and the step of sensing impedance includes determining the complex impedance by measuring the voltage across the isolation resistor and quadrature sampling.

10. The method of claim 7, wherein, muscle tissue is beneath adipose tissue at the target location, and the step of generating an output signal includes generating an output signal indicative of adipose tissue when the sensed impedance is relatively high and generating an output signal indicative of muscle tissue when the sensed impedance is relatively low.

11. The method of claim 10, wherein the step of inserting the needle includes inserting the needle at a target location that is spaced from the reference location a distance that is at least about two times the thickness of the adipose tissue at the reference location.

12. The method of claim 7, including the step of placing a template on the body surface such that a first opening in the template is situated at the target location and a second opening in the template defines the reference location.

13. Apparatus for identifying which of a plurality of subcutaneous tissue types a needle has penetrated at a target location through the outer surface of a body, comprising:

a reference electrode for placement on the surface of the body;

source means connectable to a syringe needle, for applying an electrical source signal to the needle;

electrical signal processing means connected to the reference electrode and to the means for applying a source signal, said processing means including means for sensing the impedance encountered by said source signal in passing between the needle and the reference electrode;

means responsive to variations in the sensed impedance for generating an output signal indicative of the type of subcutaneous tissue into which the needle has penetrated.

14. The apparatus of claim 13, wherein the source means includes one of an oscillating current or oscillating voltage generator.

15. The apparatus of claim 14, wherein the signal processing means includes an isolation resistor connected between the source means and the reference electrode, and means for determining the complex impedance by measuring the voltage across the isolation resistor with quadrature sampling.

16. The method of claim 13, wherein, the means for generating an output signal generates an output signal indicative of adipose tissue when the sensed impedance is relatively high and generates an output signal indicative of muscle tissue when the sensed impedance is relatively low.

17. The apparatus of claim 13, including a template for placement of the body, the template having a first opening for defining the target location and a second opening for defining the reference location.

* * * * *